(12) United States Patent
Moukhina

(10) Patent No.: US 9,389,194 B2
(45) Date of Patent: Jul. 12, 2016

(54) SYSTEM AND METHOD FOR ANALYSIS IN MODULATED THERMOGRAVIMETRY

(71) Applicant: NETZSCH-Geraetebau GmbH, Selb (DE)

(72) Inventor: Elena Moukhina, Selb (DE)

(73) Assignee: NETZSCH-GERAETEBAU GMBH, Selb (DE)

( * ) Notice: Subject to any disclaimer, the term of this patent is extended or adjusted under 35 U.S.C. 154(b) by 455 days.

(21) Appl. No.: 14/026,741

(22) Filed: Sep. 13, 2013

(65) Prior Publication Data

US 2015/0078415 A1 Mar. 19, 2015

(51) Int. Cl.
*G01N 25/48* (2006.01)

(52) U.S. Cl.
CPC ............................ *G01N 25/48* (2013.01)

(58) Field of Classification Search
CPC ................................ G01N 25/00; G01N 25/48
USPC ............................................................. 374/14
See application file for complete search history.

(56) References Cited

U.S. PATENT DOCUMENTS

| | | | |
|---|---|---|---|
| 4,914,297 A * | 4/1990 | Wieboldt | G01N 21/3504 250/343 |
| 5,224,775 A | 7/1993 | Reading et al. | |
| 5,346,306 A * | 9/1994 | Reading | G01N 25/18 374/10 |
| 6,113,261 A | 9/2000 | Blaine | |
| 6,336,741 B1 | 1/2002 | Blaine | |
| 2002/0041619 A1* | 4/2002 | Merzliakov | G01N 25/005 374/44 |
| 2003/0007542 A1* | 1/2003 | Peterman, Jr. | G01G 21/14 374/14 |
| 2003/0086471 A1* | 5/2003 | Nakatani | G01G 23/06 374/14 |
| 2003/0211621 A1* | 11/2003 | Rovani, Jr. | G01N 29/07 436/55 |
| 2005/0025212 A1* | 2/2005 | Carter | G01K 11/02 374/1 |
| 2006/0120431 A1* | 6/2006 | Monceau | G01N 5/04 374/14 |
| 2006/0140246 A1* | 6/2006 | Danley | G01G 19/52 374/14 |
| 2010/0241364 A1* | 9/2010 | Spannagel | G01G 17/04 702/24 |

FOREIGN PATENT DOCUMENTS

| | | |
|---|---|---|
| EP | 0559362 A1 | 9/1993 |
| EP | 0930500 A2 | 7/1999 |

OTHER PUBLICATIONS

Extended European Search Report issued in related European Application No. 14003002.4-1558, report dated Nov. 28, 2014.
Blaine, R.L. and Hahn, B.K., "Obtaining Kinetic Parameters by Modulated Thermogravimetry," Journal of Thermal Analysis, vol. 54, 1998, pp. 695-704.
Cheng, K. et al., "A modulated-TGA approach to the kinetics of lignocellulosic biomass pyrolysis/combustion," Polymer Degradation and Stability, vol. 97, No. 9, Sep. 2012, pp. 1606-1615.

* cited by examiner

*Primary Examiner* — Lisa Caputo
*Assistant Examiner* — Philip Cotey
(74) *Attorney, Agent, or Firm* — Pearne & Gordon LLP

(57) ABSTRACT

Disclosed are improved methods and apparatus for determining a kinetic parameter of a sample via thermogravimetry. According to the methods, accuracy of the measured parameter is improved and made less susceptible to noise across a temperature range, in particular at near-zero values of the rate of change of the weight of the sample. The disclosed methods avoid taking a logarithm of the first derivative of a thermogravimetric signal related to the sample weight detected during the experiment.

14 Claims, 9 Drawing Sheets

SYSTEM AND METHOD FOR ANALYSIS IN MODULATED THERMOGRAVIMETRY

FIELD OF THE INVENTION

The present invention relates to modulated thermogravimetry, and in particular to a system (e.g. an apparatus) and a method for determining a kinetic parameter of a sample by means of modulated thermogravimetry.

BACKGROUND OF THE INVENTION

Analysis method of modulated thermogravimetry, also known as modulated-temperature thermogravimetry, was introduced by R. L. Blaine and B. K. Hahn, Obtaining Kinetic Parameters by modulated Thermogravimetry, Journal of Thermal Analysis, Vol. 54 (1998) 695-704. It is used now widely as the standard method of modulated thermogravimetric analysis. It is described e.g. in Roger L. Blaine, U.S. Pat. No. 6,336,741 (2002).

Firstly, we will shortly put here the main idea of this standard method. The thermogravimetric measurements must be done under modulated temperature conditions, where the temperature is the sum of an underlying linear heating and temperature oscillations. The amplitude of the temperature oscillations is usually from 5K to 10K, which is much higher than for modulated DSC (cf. e.g. M. Reading, B. K. Hahn and B. S. Crow, U.S. Pat. No. 5,224,775 (1993)), where the typical temperature amplitude is about 0.5K. Period is usually from 60 to 300 s, underlying heating rate is usually from 1 to 20K/min.

The main kinetic equation is $$\frac{d\alpha}{dt} = Zf(\alpha)\exp\left(-\frac{Ea}{RT}\right) \quad (1)$$

wherein $\alpha$ is the degree of conversion, t is the time, Z is the pre-exponential factor, Ea is the activation energy, R is the gas constant, and T is the (absolute) temperature.

A list of these and other notations used in this description can be found at the end of the description.

If equation (1) is written twice for the same chemical process but for different conversion values $\alpha_1$ and $\alpha_2$ and correspondent temperatures $T_1$ and $T_2$ then the following equations for each reaction rate can be written:

$$\frac{d\alpha_1}{dt} = Zf(\alpha_1)\exp\left(-\frac{Ea}{RT_1}\right) \quad (2)$$

$$\frac{d\alpha_2}{dt} = Zf(\alpha_2)\exp\left(-\frac{Ea}{RT_2}\right) \quad (3)$$

Then the equations are divided by each other and the logarithm is taken:

$$\ln\left(\frac{d\alpha_1}{d\alpha_2}\right) = \ln\left(\frac{f(\alpha_1)}{f(\alpha_2)}\right) - \frac{Ea}{R}\left(\frac{1}{T_1} - \frac{1}{T_2}\right) \quad (4)$$

From this expression the activation energy can be found:

$$Ea = R*\left(\ln\left(\frac{d\alpha_1}{d\alpha_2}\right) - \ln\left(\frac{f(\alpha_1)}{f(\alpha_2)}\right)\right)\frac{T_1 T_2}{T_2 - T_1} \quad (5)$$

The so-called DTG signal, calculated as the first derivative from the thermogravimetric signal (weight change signal), has oscillations for modulated measurements. Then it is possible to draw two additional curves: A top curve $DTG_{top}$ through the peak points of modulated signal DTG, and a bottom curve $DTG_{bottom}$ through the valleys having correspondent values of reaction rates $d\alpha_2/dt$ and $d\alpha_1/dt$. If A is the temperature amplitude and $T_0$ is the underlying linear temperature, then $T_1=T_0+A$, $T_2=T_0-A$, $\alpha_1=\alpha_2$, $f(\alpha_1)=f(\alpha_2)$, and the final expression for activation energy is:

$$Ea = R*\ln\left(\frac{d\alpha_2}{d\alpha_2}\right)\frac{T^2 - A}{2A} \quad (6)$$

where the term $\ln(d\alpha_1/d\alpha_2)$ refers to the logarithm of the ratio of minimum and maximum reaction rates. More specifically, it is the amplitude of the logarithm of the first derivative of the thermogravimetric signal indicative of the weight of the sample under investigation at the particular temperature, T. Usually the published curves of activation energy, calculated by this standard method, have minimum point at the highest reaction rate and very high values of activation energy at the beginning and at the end of the reaction (cf. R. L. Blaine and B. K. Hahn, Obtaining Kinetic Parameters by modulated Thermogravimetry, Journal of Thermal Analysis, Vol. 54 (1998) 695-704; and Kun Cheng, William T. Winter, Arthur J. Stipanovic, A modulated-TGA approach to the kinetics of lignocellulosic biomass pyrolysis/combustion, Polymer Degradation and Stability Volume 97, Issue 9, September 2012, Pages 1606-1615). Sometimes these values exceed 1000 kJ/mol for polymers (cf. R. L. Blaine and B. K. Hahn, Obtaining Kinetic Parameters by modulated Thermogravimetry, Journal of Thermal Analysis, Vol. 54 (1998) 695-704), and therefore can not be considered as the activation energy in chemical sense, but rather as the numerical problems at the slow reaction rate. We can see from the above formula (6), that for very slow reaction rate where $d\alpha_1$ is about zero, the calculation of logarithm produces very high uncertainty because the logarithm function changes very fast near zero. Therefore any measurement noise for the almost-zero-signal produces very high error in the activation energy.

Problems in prior art algorithm:
1. The method needs reaction rates a, which are not too close to zero, otherwise the logarithm of ratio can not be found, because at zero the logarithm function goes to negative infinity.
2. The method needs the top curve $DTG_{top}$ and bottom curve $DTG_{bottom}$ having the same sign to have positive ratio for logarithm calculation. In reality it is not always the case.
3. The positions of the top curve and bottom curve depend on the noise, and therefore noise has big influence on the results.

If the measured data contain noise, then it is very hard to define correctly the position of the top curve $DTG_{top}$ and bottom curve $DTG_{bottom}$. For the unsmoothed data both positions depend on the noise amplitude. But the smoothing of the noise for the signal of unknown shape may distort the shape and reduce the oscillation amplitude of the measured DTG signal. Therefore the smoothing may lead to the evaluation error. Additionally the positions of the top curve and bottom curve for this method can not be determined from the Fourier analysis of only main frequency, because the shape of reaction rate signal can be far from sinus.

SUMMARY OF THE INVENTION

Disclosed herein is an alternative way to conduct a modulated thermogravimetry, and in particular to determine at least one kinetic parameter, in particular the activation energy, where the above listed problems are not present.

The main idea of the present invention is to avoid the calculation of logarithm for determining the kinetic parameter, because the logarithmic calculation produces a high error for slow reaction rates with values about zero. In particular, calculation of the logarithmic term in Eq. 6, $\ln(d\alpha_1/d\alpha_2)$, is avoided according to the invention because such logarithmic terms introduce into the solution for Ea the aforementioned drawbacks. In its broadest terms, therefore, the invention relates to apparatus and methods for calculating a kinetic parameter such as Ea from a modulated thermogravimetry experiment where a sample is subjected to a modulated temperature program, wherein determination of that parameter excludes calculating the logarithm of a non-exponential function derived from the first derivative of the thermogravimetric signal. Note that $\ln(e^{f(x)})$ simply returns $f(x)$ thus removing the logarithm from the calculation, which is why it is necessary to say that the foregoing method excludes calculating the logarithm of a non-exponential function as described here. It is to be understood that the terms "logarithm" and "non-exponential function" as used herein do not necessarily imply any particular basis, even though the base "e" is referred to above. For example, the term "logarithm" includes logarithms of any basis, including the natural logarithm where its base is "e," as well as logarithms of other bases such as 10, e.g. $\log_{10}(x)$. Separately, the term "non-exponential function" means a function that is not an exponential, regardless whether the base of the function is the base of the natural logarithm, "e," as in $e^{(x)}$, or some other base such as 10, as in $10^{(x)}$. The point is that according to the disclosed methods, determination of a kinetic parameter avoids calculation of logarithms derived from the thermogravimetric signal, whatever their base, because such terms introduce noise and other undesirable attributes into the calculated parameter.

According to a first aspect of the present invention, a system for determining a kinetic parameter of a sample includes:
an oven having a heater for heating the sample according to a modulated temperature program that has a temperature amplitude and a modulation period;
means for detecting a thermogravimetric signal corresponding to a weight of the sample;
means for determining a first derivative and amplitude of the first derivative of the thermogravimetric signal as the sample changes weight as a result of being heated according to the temperature program; and
means for determining at least one kinetic parameter using the temperature, the temperature amplitude, the first derivative of the thermogravimetric signal and the amplitude of the first derivative of the thermogravimetric signal, but without using a logarithm of a non-exponential function derived from the first derivative of the thermogravimetric signal.

According to another aspect of the invention, a method for determining a kinetic parameter of a sample includes the steps of:
heating the sample according to a modulated temperature program having a temperature amplitude and a modulation period;
detecting a thermogravimetric signal corresponding to a weight of the sample;
determining a first derivative of the thermogravimetric signal, as well as an amplitude of the first derivative of the thermogravimetric signal, as the sample changes weight in response to being heated according to the temperature program; and
determining at least one kinetic parameter using the temperature, the temperature amplitude, rate first derivative of the thermogravimetric signal and the amplitude of the first derivative of the thermogravimetric signal, but without using a logarithm of a non-exponential function derived from the first derivative of the thermogravimetric signal.

According to yet another aspect of the invention, a method of determining an activation energy of a sample of material includes the steps of:
heating the sample according to a modulated temperature program having a temperature amplitude and a modulation period;
measuring a weight of the sample as it is heated and detecting a thermogravimetric signal representative of its weight;
monitoring the thermogravimetric signal as the sample changes weight as a result of being heated according to the temperature program; and
calculating an activation energy of the sample at a particular temperature in the temperature program based on the particular temperature, the temperature amplitude at that temperature, and the first derivative of the thermogravimetric signal at that temperature, but not based on a logarithm of a non-exponential function derived from the first derivative of the thermogravimetric signal;
wherein the activation energy calculated above is a finite value regardless of noise in the thermogravimetric signal even when the first derivative thereof is or approaches zero.

According to a preferred embodiment of the invention, the temperature program is also characterized by an underlying heating rate.

According to an embodiment, a first portion of the temperature program is characterized by an underlying heating rate and a second portion of the temperature program is characterized by quasi-isothermal operation.

According to an embodiment, the heating of the sample is modified in accordance with the rate of weight change.

Preferably, the kinetic parameter, or one of the kinetic parameters to be determined, is the activation energy (Ea).

DETAILED DESCRIPTION OF THE INVENTION

Apparatus

In general, a thermogravimetric apparatus measures the weight change of a sample (TG signal and/or DTG signal) as the function of the time and/or temperature. It usually contains a measurement cell for the sample, an oven for the heating of this cell, a thermal balance for the registration of the sample weight change, a device to control the sample temperature, and a device for the measurement and registration of the sample temperature. Conventional means for measuring and tracking both the weight and the temperature of the sample as a function of time can be used. For example, a conventional balance or other known or suitable sensor can be used to measure the sample weight. Other conventional contact or non-contact temperature-measurement methodologies for measuring temperature can be used.

Usually the temperature program is given by the operator of the instrument and has a typical temperature range from −200° C. to 1000° C. and typical heating rates from 1 to 20K/min. Temperature program can contain several segments with linear or non-linear heating and cooling or isothermal conditions.

The present invention concerns the analysis method for determination of a kinetic parameter as the activation energy for the situation, where the temperature program has an oscillating part. During the measurement the sample can change its weight because of different reasons: decomposition, evaporation, changing of magnetic properties etc. The weight change is registered by the thermal balance and the measured sample temperature is collected as the measured time-dependent signals (TG and/or DTG signal). These measured data can be passed directly to a computer for the presentation and analysis, or they can be stored in order to analyse them later by means of a dedicated analysing device of the system.

Figure 1:
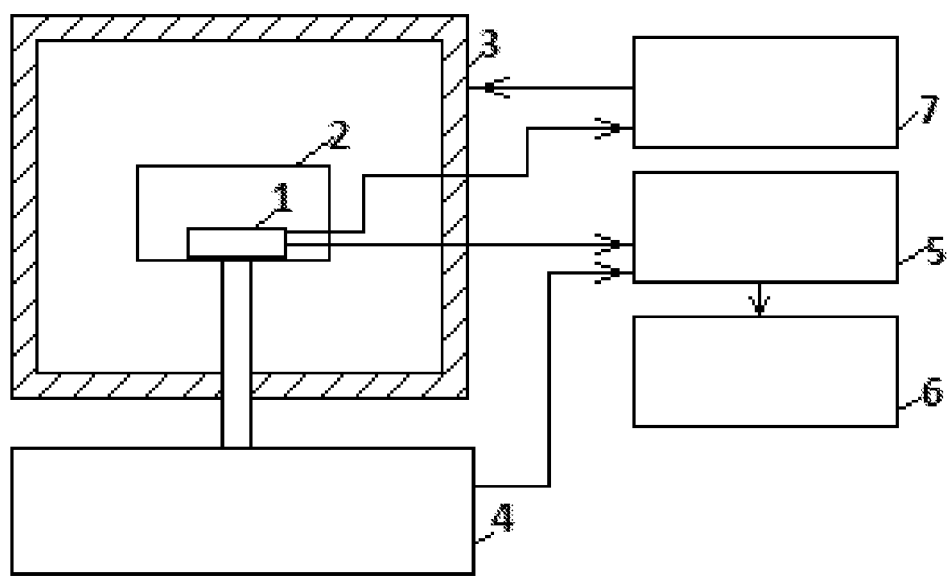
FIG. 1 shows an example of an apparatus for thermogravimetric measurement, incorporating also analysis means for determining the activation energy.

FIG. 1 shows a main structure of an example of a system for conducting a modulated thermogravimetry with determination of the activation energy Ea.

A sample 1 is placed into a measuring cell 2. The cell 2 is heated by a furnace 3, controlled by a temperature controller 7, which uses the measured sample temperature. The change of the weight is measured by a thermal balance 4. The data of the temperature signal and weight signal are gathered by an electronic device 5 and passed to a personal computer 6.

In this example, the computer 6 conducts the determination of the activation energy of the sample 1 according to the method of the invention, as more detailedly described below.

Direct Analysis Method

The basis of the "direct analysis" method is to make a direct Fourier analysis of the DTG signal. Then it will be possible to find the activation energy Ea not from the hard-defined top and bottom envelope curves $DTG_{top}$ and $DTG_{bottom}$, but directly from the well-defined amplitude $A_{DTG}$ of the main frequency in the DTG signal, which is independent of or only slightly dependent on noise.

Let us substitute modulated temperature $T=T_0+A\sin(\omega t)$ into the above main equation (1), where $T_0$ is the underlying linear temperature, A is the temperature amplitude, w is the temperature modulation frequency. For example, for a temperature amplitude of 5K and a temperature of 500K the ratio $A/T_0$ is 1%, which can be considered as a "small parameter". The $3^{rd}$ term in series is 1E-6 and in most cases is under the instrument error in the thermogravimetric (TG) signal, which has the lowest value typically about 1E-5, corresponding to 0.1 μg for 10 mg mass change.

Thus, the usual accuracy of TG measurement allows to create the series only up to the $3^{rd}$ degree:

$$\frac{d\alpha}{dt} = Zf(\alpha)\exp\left(-\frac{Ea}{RT_0}\right)*(1+S_1\sin\omega t+S_2(\sin\omega t)^2+S_3(\sin\omega t)^3) \quad (7)$$

$$S_1 = \frac{Ea}{RT_0^2}A \quad (8)$$

$$S_2 = \frac{Ea(Ea-2RT_0)}{2R^TT_0^4}A^2 \quad (9)$$

$$S_3 = \frac{Ea(Ea^2-6EaRT_0+6R^2T_0^2)}{6R^3T_0^6}A^3 \quad (10)$$

We apply the Fourier analysis for formula (3) and get the Fourier series:

$$\frac{d\alpha}{dt}=Zf(\alpha)\exp\left(-\frac{Ea}{RT_0}\right)* \quad (11)$$
$$\left(\left(1+\frac{S_2}{2}\right)+\left(S_1+\frac{3S_3}{4}\right)\sin\omega t-\frac{S_2}{2}\cos 2\omega t-\frac{S_3}{4}\sin 3\omega t\right)$$

The amplitude for the each frequency can be well-defined from experiment, even when noise is present. There are two different solutions: A simple case for linear response and an advanced solution for the non-linear response.

Linear Response

For a small temperature amplitude A the response in the DTG signal is linear, and the shape of the DTG signal is very close to sinus. The corresponding equation contains only term $S_1$, all next terms are non-linear regarding temperature amplitude A. The resulting equation is very simple:

$$\frac{d\alpha}{dt}=Zf(\alpha)\exp\left(-\frac{Ea}{RT_0}\right)\left(1+\frac{Ea}{RT_0^2}A\sin(\omega t)\right) \quad (12)$$

The non-oscillating part of the reaction rate can be calculated as the average over the modulation period. The average reaction rate here is exactly equal to the reaction rate from equation (1) for the measurement without modulation. The expression for non-oscillating part is described as $$\left(\frac{d\alpha}{dt}\right)_0 = Zf(\alpha)\exp\left(-\frac{Ea}{RT_o}\right) \quad (13)$$

It can be calculated at each point as the average over period. Amplitude of the reaction rate signal then can be written as the expression $$A_{d\alpha/dt} = \left(\frac{d\alpha}{dt}\right)_0 \frac{Ea}{RT_0^2} A \quad (14)$$

In the terms of thermogravimetry we write amplitude $A_{DTG}$ of DTG signal as the function of the absolute value from average $DTG_0$:

$$A_{DTG} = |DTG_0| \frac{Ea}{RT_0^2} A \quad (15)$$

where $DTG_0$ is the average of DTG over period for the underlying temperature $T_0$ and $|DTG_0|$ is the absolute value of $DTG_0$. The averaging range for the point $T_0$ starts half of period before $T_0$ and finishes half of period after $T_0$. $A_{DTG}$ is the amplitude of DTG signal. Within the present invention, it can be found from the measured data by using discrete Fourier analysis.

From formula (15) we can conclude in linear approximation: In the modulated thermogravimetric measurement the amplitude of DTG signal is proportional to the temperature amplitude A, average $DTG_0$ value, and the current activation energy Ea of the process. We can introduce a normalized amplitude $A_{norm}$, calculated directly from the well-defined amplitude $A_{DTG}$ of the main frequency for DTG:

$$A_{norm} = \frac{1}{A} \frac{A_{DTG}}{|DTG_0|} \quad (16)$$

With this substitution, the activation energy Ea can be expressed as:

$$Ea = A_{norm} RT_0^2 \quad (17)$$

Thus, according to the present invention, the activation energy Ea can be determined on basis of above formula (17), i.e.: $Ea=(RT_0^2 A_{DTG})/(A|DTG_0|)$. This formula can be advantageously applied for the situations where the shape of the modulated thermogravimetric signal is very close to the sinus. In the inventive system, the means for determining at least one kinetic parameter can be implemented as a computing means for conducting the calculation according to formula (17). Notably, formula (17) above does not involve or require calculation of the logarithm of any non-exponential function as discussed above.

Non-Linear Response: Non-Oscillating Part

The average over the period for modulated reaction rate is described by the non-oscillating part from formula (11):

$$\left(\frac{d\alpha}{dt}\right)_0 = Zf(\alpha)\exp\left(-\frac{Ea}{RT_0}\right) * \left(1 + \frac{1}{2}\frac{Ea(Ea-2RT_0)}{2R^2T_0^4}A^2\right) \quad (18)$$

The formula (18) shows that the average reaction rate for the modulated measurement is faster than the reaction rate without modulations. Average reaction rate increases non-linearly with the temperature amplitude, and the reaction finishes much earlier. The reason of such behaviour is the non-linearity of the reaction rate response on the temperature changes. For example, increasing of the temperature by 10K empirically leads to an increase of reaction rate by two to four times, and the average reaction rate for periodically changing temperature signal will be higher than for non-periodic one. The decreasing of reaction temperature by 10K leads to the decreasing of reaction rate by the same factor. According to expression (18) we can conclude that the applying of the temperature modulation with the amplitude $T_0$ increases the average reaction rate by the factor $$\left(1 + \frac{1}{2}\frac{Ea(Ea-2RT_0)}{2R^2T_0^4}A_0^2\right) \quad (19)$$

From the formula (11) we find the amplitude of the second harmonic of reaction rate:

$$A_2 = Zf(\alpha)\exp\left(-\frac{Ea}{RT_0}\right) * \frac{S_2}{2} \quad (20)$$

and the non-oscillating reaction rate:

$$\left(\frac{d\alpha}{d\tau}\right)_0 = Zf(\alpha)\exp(-Ea/RT_0)) \quad (21)$$

The ratio of these two expressions is equal to $S_2/2$. In another words, the applying of temperature modulation increases the average reaction by the factor $$\left(1 + \frac{A_2}{(d\alpha/dt)_0}\right).$$

In the terms of thermogravimetry this factor writes as $$\left(1 + \frac{A_{2DTG}}{|DTG_0|}\right),$$

where $A_{2DTG}$ is the amplitude of the second harmonic for DTG signal.

Non-Linear Response: Oscillating Part

From the equation (11) we can write the amplitude of reaction rate $A_{d\alpha/dt}$ for the first harmonic $$A_{\frac{d\alpha}{dt}} = Zf(\alpha)\exp\left(-\frac{Ea}{RT_0}\right) * \frac{Ea}{RT_0^2}A\left(1 + \frac{(Ea^2 - 6EaRT_0 + 6R^2T_0^2)}{8R^8T_0^4}A^2\right) \quad (22)$$

The non-linear part shows that the amplitude of the first harmonic increases non-linearly with the temperature amplitude. Let us divide equation (22) by (18).

$$\frac{A_{\frac{da}{dt}}}{\left(\frac{da}{d\tau}\right)_0} = \frac{Ea}{RT_0^2}A\left(\frac{8R^2T_0^4 + (Ea^2 - 6EaRT_0 + 6R^2T_0^2)A^2}{8R^2T_0^4 + 2Ea(Ea - 2RT_0)A^2}\right) \quad (23)$$

From (8) the activation energy is found:

$$Ea = A_{norm}RT_0^2\left(1 + \frac{(Ea^2 + 2EaRT_0 - 6R^2T_0^2)A^2}{8R^2T_0^4 + (Ea^2 - 6EaRT_0 + 6R^2T_0^2)A^2}\right) \quad (24)$$

It seen here that the for sinus-shaped DTG signal only linear part is important. The linear part of this formula is in agreement with (17). We put Ea from (24) iteratively into non-linear part of (24) and get the result with the accuracy of $A^2$:

$$Ea = A_{norm}RT_0^2\left(1 + \frac{A^2}{8T_0^2}(A_{norm}^2T_0^2 + 2A_{norm}T_0 - 6)\right) \quad (25)$$

Thus, according to the present invention, the activation energy can also be determined on basis of above formula (25). This formula can be advantageously applied for the situations where the shape of the modulated thermogravimetric signal is remarkably deviating from the ideal sinus shape. In the inventive system, the means for determining at least one kinetic parameter can be implemented as a computing means for conducting the calculation according to formula (25). Again, formula (25) notably does not involve or require calculation of the logarithm of any non-exponential function as discussed above.

Data for Analysis

For a verification test comparing the known and the inventive analysis methods, several simulated data sets are used. All simulations are done by direct integration of formula (1) for the first-order reaction with pre-exponential factor 1E10 s$^{-1}$, activation energy 100 kJ/mol, underlying heating rate 1 K/min, initial temperature 80° C., Period 60 seconds and temperature amplitudes 5 and 20K. In the simulation we used 50 data points per period.

Figure 2:
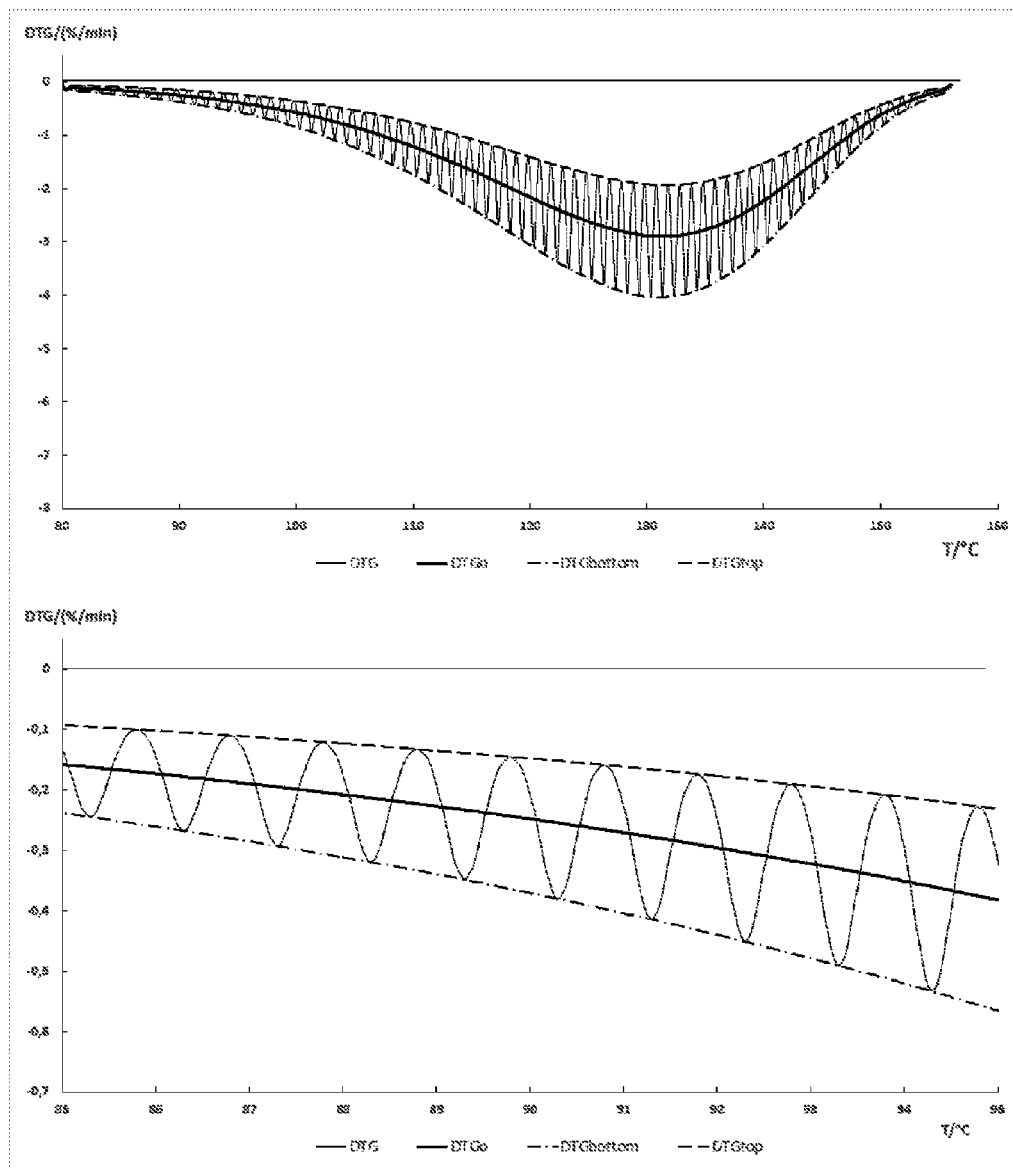
FIG. 2-5 show simulated DTG signals for different temperature amplitudes and different noise for the total and for the initial temperature ranges as the function of the underlying temperature.
Figure 3:
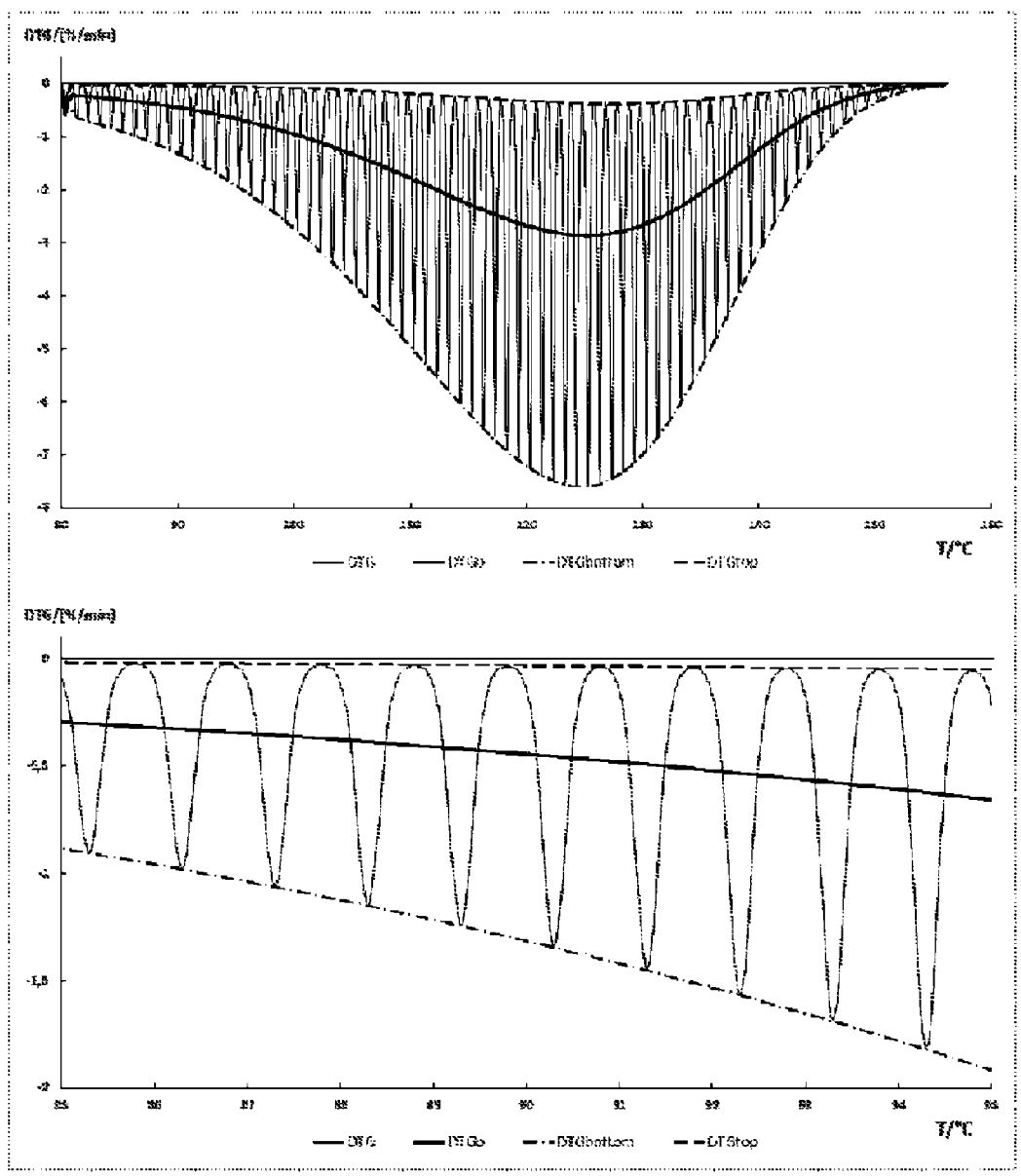

The first simulation set contains no noise, the simulated modulated curves together with the average, top and bottom curves are shown in the FIGS. 2 and 3 for the whole temperature range and for the temperature range between 85 and 95° C.

FIGS. 2 and 3 show simulated DTG signals in %/min for the first-order reaction with a pre-exponential factor 1e10 s$^{-1}$, activation energy 100 kJ/mol and temperature amplitudes 5 and 20K, without noise. Curves are simulated periodic signal, average, top curve, bottom curve.

In FIGS. 2 and 3, the lower portions each show the data from the respective upper portion for a temperature range of particular interest, in the shown example from 85 to 95° C.

The data for the temperature amplitudes 5K have the shape visually close to the sinus. We can neglect the non-linear part of the amplitude and therefore assume that here the response is linear. But for the high temperature amplitude 20K the signal is definitely not sinus-shaped. For this amplitude the lower part of the signal for each period is very sharp, and the upper part is more wide and round. The average red curve is not in the middle between the top curve and bottom curve. Therefore the data with temperature amplitude 20K may not be considered as sinus-shaped. For the amplitude of 20K the top curve is very close to zero. It means that for the real experiment containing noise, the logarithm of it can produce the high error in results.

The second simulated data set used in the verification test contains the noise of TG measurement. Mathematically we add to each calculated conversion value from the first data set the random value (from 0 to 1), multiplied by the amplitude of conversion noise. The second data set contains the simulations of the modulated reaction rate for the temperature amplitudes 5K and 20K, each with noise. The random conversion noise for the second set has amplitude of 2e-5. For the mass change of 5 mg this noise corresponds to the 0.1 μg, which is about the real noise of thermogravimetric instruments.

Figure 4:
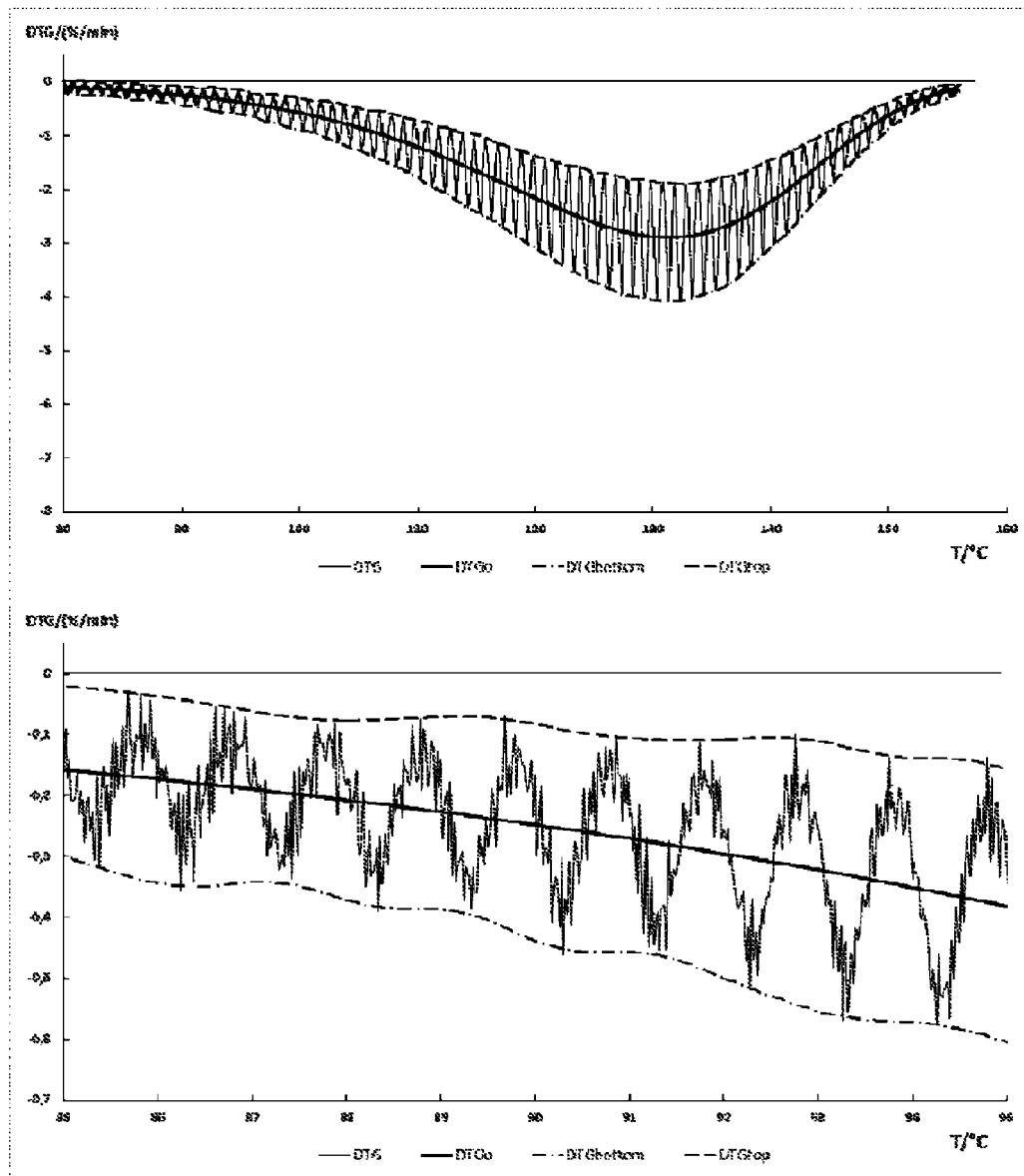
Figure 5:
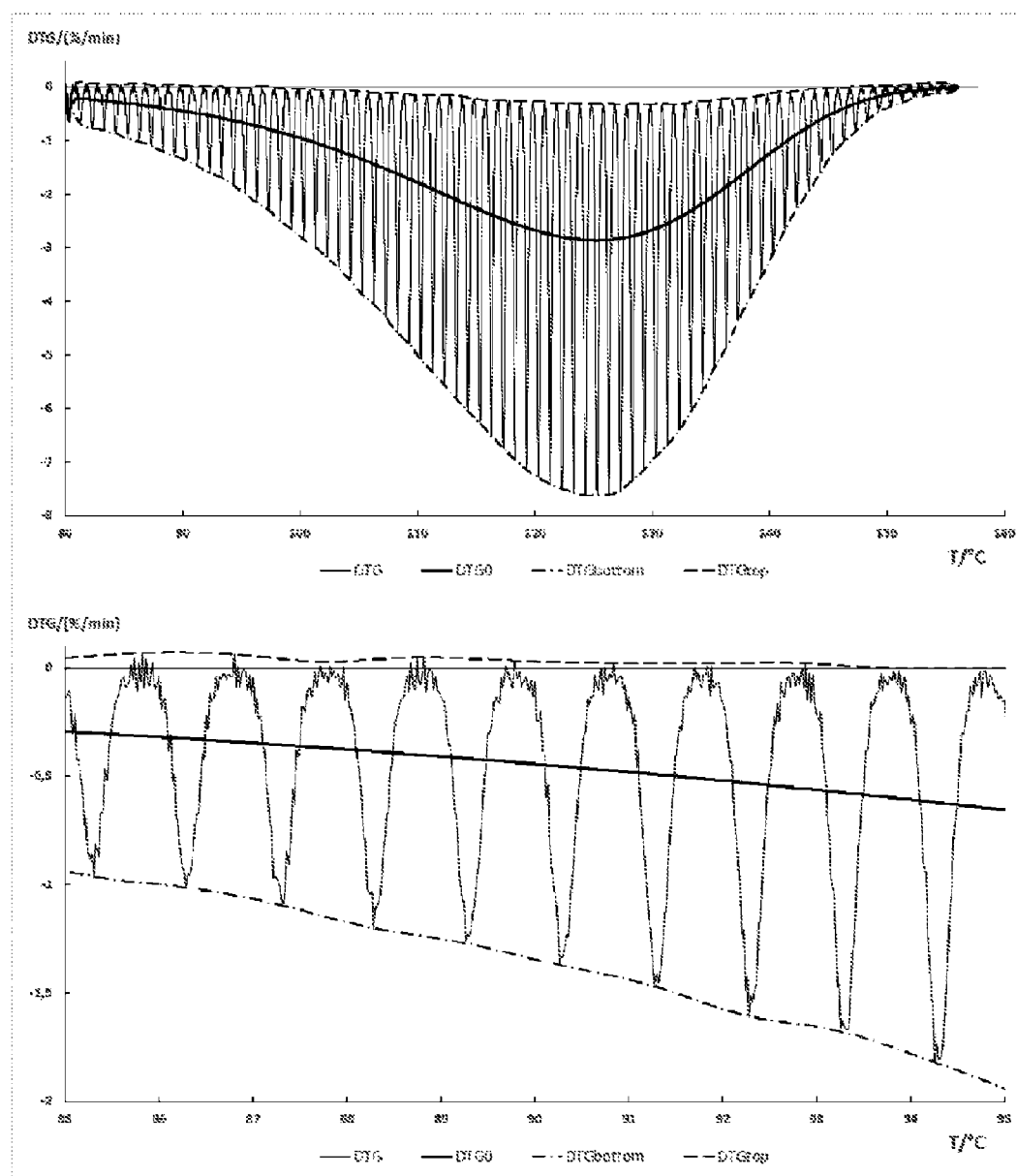

FIGS. 4 and 5 show these simulated data for temperature amplitudes of 5K and 20K, with present noise amplitude of 2E-5, for the whole range (upper portion in the figures) and short range (lower portion in the figures). The top curve DTG$_{top}$ is sometimes above zero just because of the noise, and therefore the known standard method with use of the logarithm of ratio of reaction rates does not work here.

We will apply the standard calculation of above formula (6) and the new analysis using formula (17) and formula (24) according to the invention to these data sets. If the formula (6) works well, then we expect that the resulting curves of activation energy Ea will be the constant of 100 kJ/mol for the whole reaction range. If the noise has some influence on the results, then we will see it in the deviation of the calculated activation energy from the original value 100 kJ/mol.

Results: Linear Response

Let us calculate activation energy Ea by the new method according to the formula (17) and compare with the standard calculations according to the formula (6). Formula (17) works only for the sinus-shaped signals, therefore can be applied for data with the temperature amplitude up to 5K (see e.g. FIG. 3).

Figure 7:
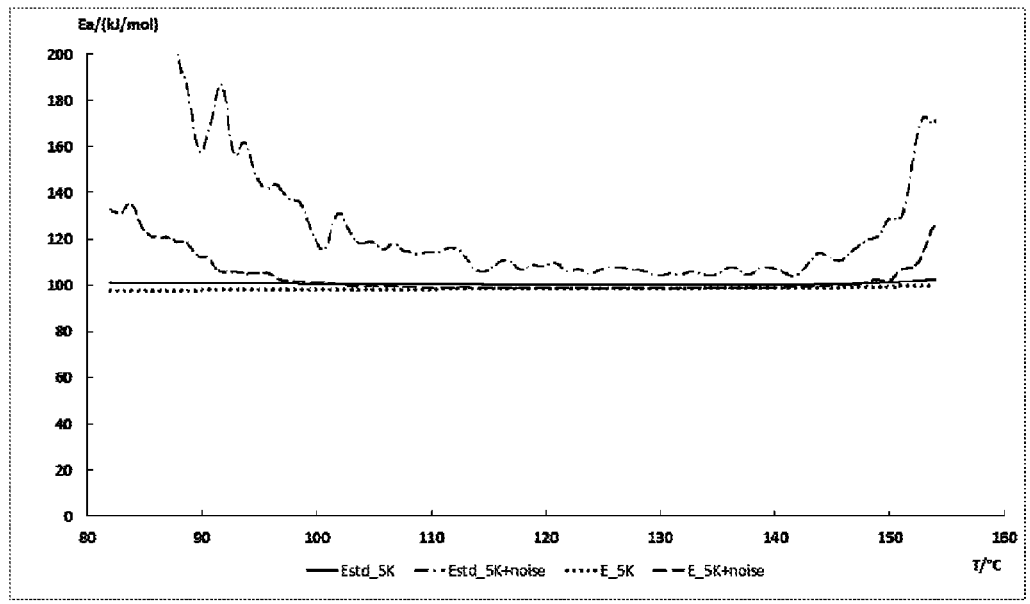
FIG. 7 shows activation energies calculated by the known standard method (Estd) and a new linear method (E) according to an embodiment of the invention, for the simulated curves with temperature amplitude 5K without noise, and with noise 2E-5.

Results of calculation for 5K for the standard method (E$_{std}$, calculated with formula (2)) and new linear method (E, calculated with formula (5)) are shown in the FIG. 7.

FIG. 7 shows activation energies Ea calculated by the standard method (E$_{std}$) and the new linear method (E) for the simulated curves with temperature amplitude 5K without noise, and with noise 2E-5.

For both amplitudes and both methods, we have everywhere good agreement between the activation energy for the data without noise and the activation energy value 100 kJ/mol, used for the calculation. The influence of the noise on the error in activation energy for the new linear method is everywhere much lower, than for the standard method. For the amplitude 5K with noise the error of the new method is at least 4-5 times less than for the standard method. For noise 2e-5 the resulting curve according to the current method of formula (17) has range from 100 to 150° C. with correct value of Ea (from 100 to 105 kJ/mol), whereas the standard calculation method produces incorrect results higher than 105 kJ/mol almost everywhere.

Results Non-Linear Response: Non-Oscillating Part

For verification of formula (18), we take modulated signal for temperature amplitudes 10K and 20K, and calculate an average for it. The resulting curves are shown in the FIG. 6 with name α$_0$. Additionally we calculate only non-oscillation part direct according to the formula (18) for both temperature amplitudes, and show resulting curves in FIG. 6 with the names α$_{new}$.

Figure 6:
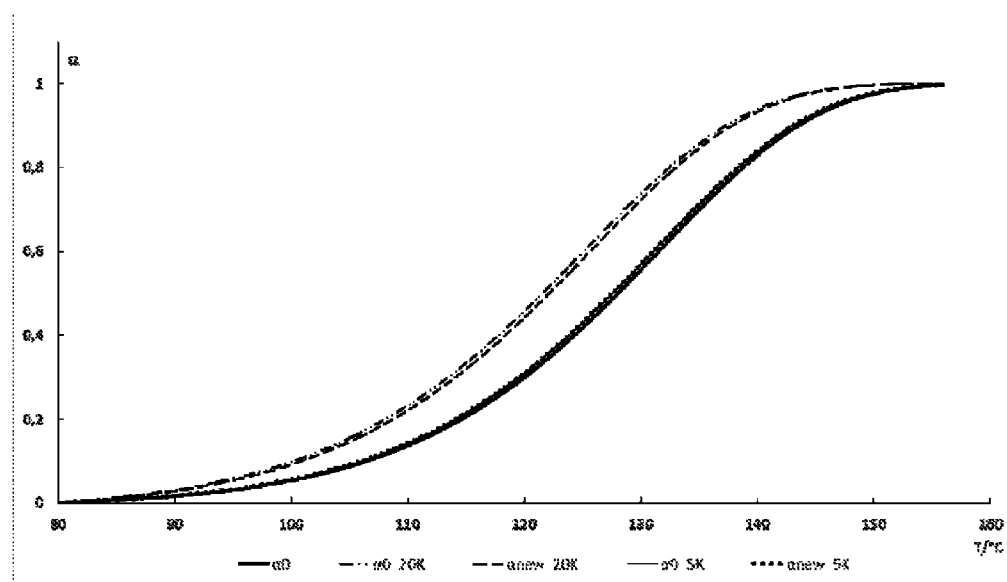
FIG. 6 shows a simulation of conversion, i.e. a degree of conversion as the function of the underlying temperature.

Thus, FIG. 6 shows a simulation of conversion: α$_0$ no oscillations (calculated by formula (1)); α$_{0\_5K}$ and α$_{0\_20K}$— average for modulated signal calculated by formula (1) for temperature amplitudes 5K and 20K; $\alpha_{new}$—direct calculation of non-oscillation part of modulated signal, according to formula (18).

We have the perfect agreement between $\alpha_0$ and $\alpha_{new}$ for both temperature amplitudes. The curve $\alpha_0$ shows the conversion for the reaction without modulation in order to see the difference between this curve and conversion curve for modulated reactions.

Non-Linear Response: Oscillating Part

Figure 8:
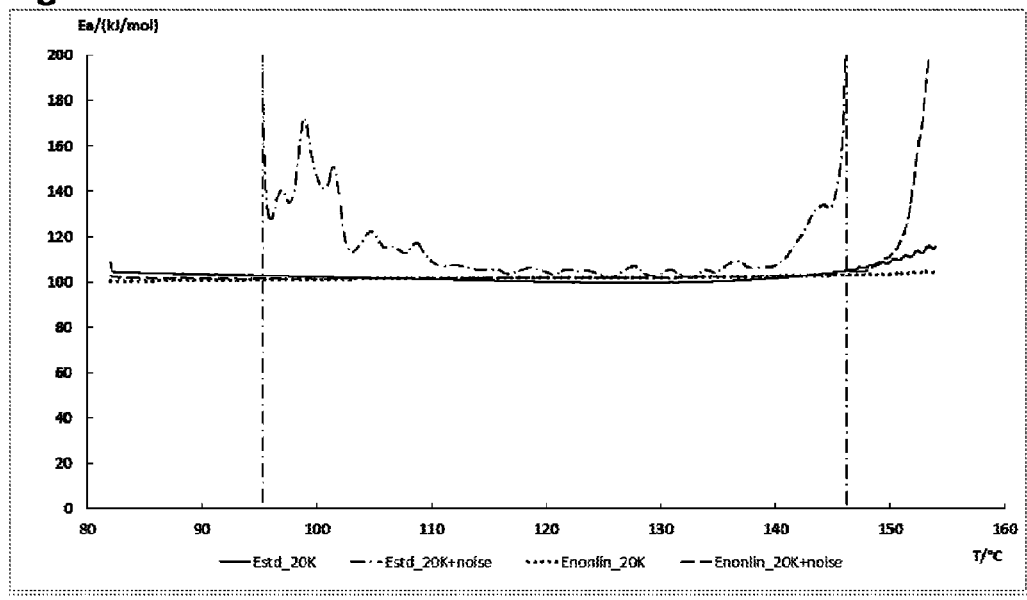
FIG. 8 shows activation energies calculated by the known standard method (Estd) and a new non-linear method (Enonlin) according to an embodiment of the invention, for the simulated curves with temperature amplitude 20K without noise, and with noise 2E-5.

FIG. 8 shows the results of second iteration for the noise 2E-5 and amplitude 20K. For the simulation, 100 kJ/mol was used again as the value for the activation energy Ea, and therefore this value is expected also as the result after analysis.

Thus, FIG. 8 shows activation energies Ea calculated by the known standard method ($E_{std}$) and the current inventive non-linear method ($E_{nonlin}$) for the previously simulated DTG curves with temperature amplitude A=20K without noise, and with noise 2E-5.

For the data without noise both methods produce correct results for each of the two temperature amplitudes used in the verification test. Only for the temperature amplitude 20K there is the light problem for the calculation of the activation energy Ea, especially at the end of the reaction, where the top curve $DTG_{top}$ is very close to zero.

For both amplitudes the noise plays a big role for the standard calculation and produces correct results only for the short time range in the middle of reaction. But at the beginning and at the end of reaction the calculated values of activation energy Ea are very far from the expected value of 100 kJ/mol. In contrast, the inventive method produces results for Ea of the same accuracy always for the wider range.

In the standard method the errors are independent of the temperature amplitude A. In the inventive method, however, the errors reduce with the temperature amplitude A. For the high noise we have the best results calculated by the inventive method for temperature amplitude of A=20K.

The results of the current inventive method have always the better agreement with the value 100 kJ/mol, which was used for data simulation. For the very high temperature amplitude of 20K the noise has a big influence on the results especially close to the beginning and the end of the measurement range, because the DTG signal is close to zero, and small noise causes the big changes in the logarithm value and therefore in the results of Ea. The noise has almost no influence on the results calculated by current method.

The main advantage of this method is present for the amplitude 20K and high noise, where the top curve $DTG_{top}$ of DTG signal is positive (See e.g. FIG. 5) and the ratio $DTG_{top}/DTG_{bottom}$ is negative. This is for the temperatures before 95° C. and after 147° C.

The known standard method using formula (2) with the logarithm calculation of this ratio can not be applied here, because the logarithm of the negative values is not defined. But the current method is advantageously able to calculate activation energy Ea also for these ranges, and the resulting value of Ea almost for the whole reaction range (in the shown example ranging from 80 to 150° C.) is very close to constant and has values from 100 kJ/mol to 110 kJ/mol.

Advantages of the Current Method According to the Invention:

1. Method calculates correct activation energy Ea also for noisy modulated DTG curves.
2. The influence of the noise on the results in current method is much lower than in the known standard method.
3. Current method can calculate activation energy also for the situations, where top and bottom curves $DTG_{top}$ and $DTG_{bottom}$ have opposite signs and thus the standard method fails.
4. The amplitude $A_{DTG}$ for the main frequency, used for calculation, can be well-defined from experiment by discrete Fourier analysis even when noise is present.

Experiment

The measurement was done on the measurement device NETZSCH STA449F3 having the modulated DSC functionality. Temperature amplitude 5K, underlying heating rate 1K/min, period 200 s. The measured results for TG and DTG signal for the second step of decomposition of CaOx monohydrate are shown in the FIG. 9.

Figure 9:
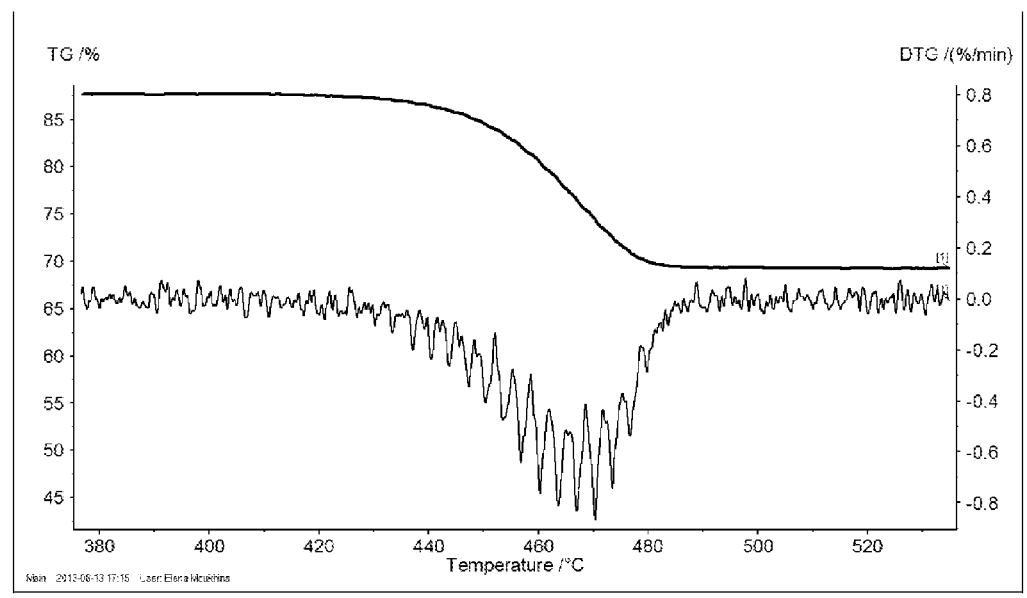
FIG. 9 shows measured thermogravimetric data, i.e. a thermogravimetric signal (TG signal) and its first derivative (DTG signal).

FIG. 9 shows this measured thermogravimetric data.

The calculations for evaluating the measurement result of FIG. 9 are done manually by the known standard and the current inventive method using formula (14).

Figure 10:
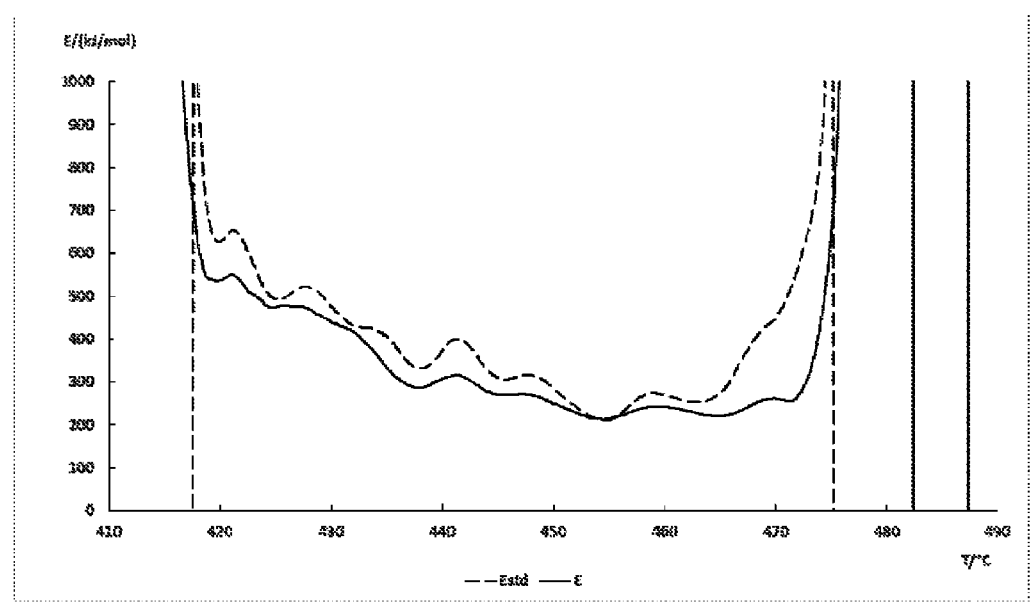
FIG. 10 shows a result of the determination of the activation energy evaluated from the data of FIG. 9, according to the known standard method (Estd), and according to an embodiment of the invention (E).

FIG. 10 shows evaluated thermogravimetric data. At T=473° C. the activation energy Ea from the current method is 210 kJ/mol, from the standard method 450 kJ/mol. This is more than twice higher. Furthermore, the current method has lower and more horizontal curve portions for the activation energy Ea. The common point is at T=455° C. with activation energy 202 kJ/mol. This corresponds to the literature values.

Further Features and Advantages of the System And Method According to the Invention 1. In linear approximation the amplitude $A_{DTG}$ of the derivative of modulated TG signal is proportional to its non-oscillation part $DTG_0$, to the temperature amplitude A, and to the current activation energy Ea of the process.
2. The average reaction rate for the modulated measurement is faster than the reaction rate without modulations, the modulation increases the average reaction by the factor $(1+A^2 DTG/|DTG_0|)$, depending on the amplitude of the second harmonic of DTG signal.
3. The method is proposed, where the activation energy Ea can be found directly from the main amplitude $A_{DTG}$ or $A_{norm}$, respectively, of the modulated DTG signal.
4. Proposed method can calculate activation energy Ea in particular for noisy measurement result curves, with better accuracy than the standard method.
5. Proposed method can calculate activation energy Ea in particular for situations, where top and bottom curves $DTG_{top}$ and $DTG_{bottom}$ have opposite signs and the standard method fails.

In summary, the invention proposes a novel analysis method for modulated thermogravimetry measurement results. The method is mathematically based on the direct Fourier analysis and can calculate the activation energy signal for the modulated thermogravimetric measurement. The method produces correct results also for noisy measurements where standard calculation method fails.

Notations:

A temperature amplitude
$A_2$ Amplitude of the second harmonic for reaction rate
$A_{DTG}$ Amplitude of DTG; amplitude of the rate of weight change
$A_{2DTG}$ Amplitude of the second harmonic for DTG
$A_{norm}$ normalized amplitude of DTG
DTG first derivative from thermogravimetric signal; rate of weight change
$DTG_0$ averaged DTG
$|DTG_0|$ absolute value of $DTG_0$
$DTG_{top}$ top curve through the maximum points of modulated signal $DTG_{bottom}$ bottom curve through the valleys of modulated signal
Ea activation energy
T absolute temperature, K
$T_0$ absolute underlying temperature, K
$T_i$ absolute temperature of the state i, K
R gas constant
t time
f(α) Function of reaction type
$S_1, S_2, S_3$ series coefficients
Z Pre-exponential factor
α Degree of conversion
$α_i$ Degree of conversion of the state i
$α_{new}$ non-oscillating part of reaction rate for modulated signal calculated by Eq. 18
ω Modulation frequency
Subindex
0 non-oscillation part of the signal

What is claimed is:

1. A system for determining a kinetic parameter of a sample, comprising:
an oven having a heater for heating the sample according to a modulated temperature program, said modulated temperature program having a temperature amplitude and a modulation period;
means for detecting a thermogravimetric signal corresponding to a weight of said sample;
means for determining a first derivative and amplitude of the first derivative of said thermogravimetric signal as said sample changes weight as a result of being heated according to said temperature program; and
means for determining at least one kinetic parameter using the temperature, the temperature amplitude, the first derivative of said thermogravimetric signal and the amplitude of the first derivative of said thermogravimetric signal, but without using a logarithm of a non-exponential function derived from the first derivative of the thermogravimetric signal.

2. The system recited in claim 1, wherein the temperature program also has an underlying heating rate.

3. The system recited in claim 1, wherein a first portion of the temperature program has an underlying heating rate and a second portion of the temperature program exhibits quasi-isothermal operation.

4. The system recited in claim 1, further comprising means for modifying the heating of the sample in accordance with the first derivative of said thermogravimetric signal.

5. The system recited in claim 1, wherein the kinetic parameter is the activation energy.

6. The system recited in claim 5, wherein the activation energy is determined by the following formula:

$$Ea=(RT_0^2 A_{DTG})(A DTG_0), \text{ wherein}$$

Ea is the activation energy,
R is the gas constant,
$T_0$ is the absolute underlying temperature,
$A_{DTG}$ is the amplitude of the first derivative of the thermogravimetric signal,
A is the temperature amplitude of the modulated temperature program, and
$DTG_0$ is an average of the first derivative of the thermogravimetric signal over the modulation period.

7. The system recited in claim 5, wherein the activation energy is determined by the following formula:

$$Ea=A_{norm}RT_0^2(1+A^2/(8T_0^2))\times(A_{norm}T_0^2+2A_{norm}T_0-6)), \text{ wherein}$$

Ea is the activation energy,
R is the gas constant,
$T_0$ is the absolute underlying temperature,
A is the temperature amplitude of the modulated temperature program, and $$A_{norm}=(1/A)\times(A_{DTG}/DTG_0), \text{ wherein}$$

$A_{DTG}$ is the amplitude of the first derivative of the thermogravimetric signal,
$DTG_0$ is an average of the first derivative of the thermogravimetric signal over the modulation period.

8. A method for determining a kinetic parameter of a sample, comprising the steps of:
heating the sample according to a modulated temperature program, said modulated temperature program having a temperature amplitude and a modulation period;
detecting a thermogravimetric signal corresponding to a weight of said sample;
determining a first derivative of said thermogravimetric signal, as well as an amplitude of said first derivative of said thermogravimetric signal, as said sample changes weight in response to being heated according to said temperature program; and
determining at least one kinetic parameter using the temperature, the temperature amplitude, the first derivative of said thermogravimetric signal and the amplitude of the first derivative of said thermogravimetric signal, but without using a logarithm of a non-exponential function derived from the first derivative of said thermogravimetric signal.

9. The method recited in claim 8, wherein the temperature program also has an underlying heating rate.

10. The method recited in claim 8, wherein a first portion of the temperature program has an underlying heating rate and a second portion of the temperature program exhibits quasi-isothermal operation.

11. The method recited in claim 8, further comprising the step of modifying the heating of the sample in accordance with the first derivative of said thermogravimetric signal.

12. The method recited in claim 8, wherein the kinetic parameter is the activation energy.

13. The method recited in claim 12, wherein the activation energy is determined by the following formula:

$$Ea=(RT_0^2 A_{DTG})/(A|DTG_0|), \text{ wherein}$$

Ea is the activation energy,
R is the gas constant,
$T_0$ is the absolute underlying temperature,
$A_{DTG}$ is the amplitude of the first derivative of the thermogravimetric signal,
A is the temperature amplitude of the modulated temperature program, and
$DTG_0$ is an average of the first derivative of the thermogravimetric signal over the modulation period.

14. The method recited in claim 12, wherein the activation energy is determined by the following formula:

$$Ea=A_{norm}R_0^2(1+A^2/(8T_0^2))\times(A_{norm}T_0^2+2A_{norm}T_0-6)), \text{ wherein}$$

Ea is the activation energy,
R is the gas constant,
$T_0$ is the absolute underlying temperature,
A is the temperature amplitude of the modulated temperature program, and $$A_{norm}=(1/A)\times(A_{DTG}/|DTG_0|), \text{ wherein}$$

$A_{DTG}$ is the amplitude of the first derivative of the thermogravimetric signal, and
$DTG_0$ is an average of the first derivative of the thermogravimetric signal over the modulation period.

* * * * *